(12) United States Patent
Collins (10) Patent No.: US 9,339,393 B2
(45) Date of Patent: May 17, 2016

(54) ORTHOPEDIC IMPLANT INSERTION INSTRUMENT

(75) Inventor: James S. Collins, Fort Wayne, IN (US)

(73) Assignee: Zimmer, Inc., Warsaw, IN (US)

(*) Notice: Subject to any disclaimer, the term of this patent is extended or adjusted under 35 U.S.C. 154(b) by 462 days.

(21) Appl. No.: 13/173,667

(22) Filed: Jun. 30, 2011

(65) Prior Publication Data
US 2012/0253469 A1    Oct. 4, 2012

Related U.S. Application Data (60) Provisional application No. 61/468,386, filed on Mar. 28, 2011.

(51) Int. Cl.
| | | |
|---|---|---|
| *A61F 2/02* | (2006.01) | |
| *A61B 17/58* | (2006.01) | |
| *A61F 2/46* | (2006.01) | |
| *A61F 2/30* | (2006.01) | |

(52) U.S. Cl.
CPC .............. *A61F 2/4603* (2013.01); *A61F 2/4607* (2013.01); *A61F 2002/30471* (2013.01); *A61F 2002/30507* (2013.01); *A61F 2002/4627* (2013.01); *A61F 2002/4628* (2013.01)

(58) Field of Classification Search
CPC ........... A61F 2/02; A61F 7/10; A61F 2/4603; A61B 19/46; A61B 17/320016; A61B 17/2909; A61B 2017/0046; A61B 2017/00477; A61B 17/320092; A61B 17/7011; A61B 17/7291; A61B 2017/00367; A61B 2017/00398; A61B 2017/681; A61B 17/0483; A61B 17/0642; A61B 17/0644
USPC ................................ 623/21.11–22.2; 606/99
See application file for complete search history.

(56) References Cited

U.S. PATENT DOCUMENTS

| | | | | |
|---|---|---|---|---|
| 5,064,427 A | * | 11/1991 | Burkinshaw | 606/99 |
| D360,686 S | | 7/1995 | Kumar et al. | |
| 5,476,466 A | * | 12/1995 | Barrette et al. | 606/86 R |
| 6,110,179 A | * | 8/2000 | Flivik | A61B 17/8808 606/94 |
| 6,113,605 A | * | 9/2000 | Storer | 606/99 |
| 6,626,913 B1 | * | 9/2003 | McKinnon et al. | 606/99 |
| 7,976,548 B2 | * | 7/2011 | Burgi et al. | 606/99 |
| 2008/0269765 A1 | | 10/2008 | Banerjee et al. | |

OTHER PUBLICATIONS

Brochure—Zimmer M/L Taper Hip Prosthesis with Kinectiv Technology, Zimmer, Inc. 2007, 2008, 2009.

* cited by examiner

*Primary Examiner* — Christopher D Prone
*Assistant Examiner* — Ann Schillinger
(74) *Attorney, Agent, or Firm* — Schwegman Lundberg & Woessner, P.A.

(57) ABSTRACT

A surgical instrument is disclosed that facilitates the implantation of one of a number of differently sized or differently configured hip stem prostheses into a proximal end of a femur while also providing a surgeon with a substantial amount of rotational control over the prosthesis during the implantation. A suitable hip stem prosthesis is selected from a family of hip stem prostheses of varying sizes and dimensions. The surgical instrument attaches to the selected hip stem prosthesis via first and second spaced engagement portions such that the instrument is operable to exert rotational control over the selected hip stem prosthesis. The first engagement portion is an impaction portion configured to engage a corresponding impaction feature on a proximal body portion of the hip stem prosthesis. The second engagement portion is an adjustable clamping portion configured to clampingly receive the neck of the hip stem prosthesis, regardless of the prosthesis size.

17 Claims, 11 Drawing Sheets

FIG_1

FIG_2

FIG_12A

FIG_12B

ORTHOPEDIC IMPLANT INSERTION INSTRUMENT

CROSS-REFERENCE TO RELATED APPLICATION

This application claims priority under Title 35, U.S.C. §119(e) to U.S. Provisional Patent Application Ser. No. 61/468,386, filed Mar. 28, 2011, the entire disclosure of which is hereby expressly incorporated by reference herein.

BACKGROUND

1. Field of Invention

The present disclosure relates to a surgical instrument, and in particular to a surgical instrument for facilitating the implantation of a prosthetic component, such as a hip prosthesis.

2. Description of Related Art

Prostheses are commonly utilized to repair and/or replace damaged bone and tissue in the human body. For example, a hip prosthesis may be implanted to replace damaged or destroyed bone in the femur and/or acetabulum and recreate the natural, anatomical articulation of the hip joint. During a total hip arthroplasty procedure, the surgeon may ream the acetabulum of a patient to prepare a reamed area for receiving an acetabular cup prosthesis, and rasp the proximal femur to provide a rasped area for receiving a femoral hip stem prosthesis that includes a stem and neck portion. The femoral stem portion includes a bone-engaging surface configured to be accepted into the rasped area of the proximal femur, and the femoral neck portion includes a head component having an articulating surface to articulate with the acetabular cup prosthesis seated within the acetabulum, for example. The articulating head component is seated atop a head region of the femoral neck portion that is utilized to secure the femoral head component to the hip stem prosthesis.

Once the femur is prepared, a femoral hip stem prosthesis having selected characteristics, such as offset and leg length dimensions, is inserted into the prepared femur. Offset and leg length dimensions as used within this disclosure are described in the Zimmer®M/L Taper Hip Prosthesis with Kinectiv® Technology brochure submitted herewith in an Information Disclosure Statement, the entire disclosure of which is hereby explicitly incorporated by reference herein. The center of the head region of the neck portion of the femoral hip stem prosthesis may be offset substantially in a medial or lateral direction with reference to a person's anatomy, for instance, from a nominal center of rotation, with the medial-lateral offset dimension determined with reference to a longitudinal axis of the femoral hip stem prosthesis. Additionally, the center of the head region may be substantially in a proximal or distal direction spaced from a nominal center of rotation along a leg length dimension aligned with the longitudinal axis of the femoral hip stem prosthesis. Leg length and offset dimensions may be determined using suitable templates together with x-ray images, for example.

Typically, a surgeon uses a surgical instrument to facilitate the implantation of a hip stem prosthesis. The utilized surgical instrument may be, for example, an inserter that assists with insertion of the hip stem prosthesis and/or an impactor that assists with seating of the prosthesis within a prepared canal of the proximal femur.

SUMMARY

The present disclosure provides a surgical instrument for facilitating the implantation of one of a number of differently sized or differently configured hip stem prostheses into a proximal end of a femur while also providing a surgeon with a substantial amount of rotational control over the prosthesis during the implantation. A suitable hip stem prosthesis is selected from a family of hip stem prostheses of varying sizes and dimensions. The surgical instrument attaches to the selected hip stem prosthesis via first and second spaced engagement portions such that the instrument is operable to exert rotational control over the selected hip stem prosthesis. The first engagement portion is an impaction portion configured to engage a corresponding impaction feature on a proximal body portion of the hip stem prosthesis. The second engagement portion is an adjustable clamping portion configured to clampingly receive the neck of the hip stem prosthesis, regardless of the prosthesis size.

The instrument includes an actuation assembly that allows adjustment of the clamping portion to clamp either a first neck portion of a first hip stem prosthesis or a second neck portion of a second, differently configured hip stem prosthesis. When the clamping portion clamps a femoral neck portion and the impaction portion of the instrument is engaged with the corresponding impaction feature of the proximal body portion of the hip stem prosthesis, the prosthesis is connected to the surgical instrument via the impaction and clamping portions. With this dual engagement, the impaction portion of the surgical instrument acts as an anchoring point while the clamping portion of the surgical instrument provides a clamping force to allow the surgical instrument to tightly clamp and control rotation of the attached hip stem prosthesis.

The present disclosure, in one form thereof, comprises a surgical instrument for use with a hip stem prosthesis, the hip stem prosthesis including a proximal body portion and a neck portion, the surgical instrument including a body, a first engagement portion engageable with the proximal body portion of the hip stem prosthesis, the first engagement portion aligned substantially along a first axis, and a second engagement portion receivable about, and engageable with, the neck portion of the hip stem prosthesis, the second engagement portion spaced from the first axis and adjustably connected to the body to vary the spacing of the second engagement portion from the first axis.

The present disclosure, in another form thereof, comprises a surgical instrument for use with a hip stem prosthesis, the hip stem prosthesis including a proximal body portion and a neck portion, the surgical instrument including first engagement means for engaging with the proximal body portion of the hip stem prosthesis, the first engagement means aligned substantially along a first axis, and second adjustable engagement means for engaging around the neck portion of the hip stem prosthesis, the second adjustable engagement means adjustable to vary the spacing of the second adjustable engagement means from the first axis.

The present disclosure, in a further form thereof, comprises a method of implanting a hip stem prosthesis, the hip stem prosthesis including a proximal body portion and a neck portion, the method including: obtaining a surgical instrument including a first engagement portion and a second engagement portion, the first engagement portion aligned substantially along a first axis; engaging the first engagement portion with the proximal body portion of the hip stem prosthesis; placing the second engagement portion around the neck portion of the hip stem prosthesis; and moving the second engagement portion towards the first axis to clamp the second engagement portion to the neck portion of the hip stem prosthesis to secure the surgical instrument to the hip stem prosthesis.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

A surgical instrument usable as an impactor and an inserter that facilitates the implantation of a hip stem prosthesis into a proximal end of a femur and which, when attached to the hip stem prosthesis, provides rotational control of the hip stem prosthesis is disclosed. The surgical instrument is able to attach to hip stem prostheses of multiple sizes and configurations, as described below. Also as described below, the surgical instrument includes a first engagement portion that is an impaction portion for engagement with a corresponding impaction feature on a proximal body portion of a hip stem prosthesis and a second engagement portion that is a clamping portion for receipt of and to clamp a femoral neck/head component of the hip stem prosthesis.

The clamping portion includes an annular engagement member or collar for engaging a tapered surface beneath the head component of the hip stem prosthesis. The annular collar is adjustable via an actuation assembly to clamp to either a first hip stem prosthesis or a second, differently sized hip stem prosthesis, as described further below. The engagement of both the clamping portion and the impaction portion allows for a rotatably controllable attachment of the prosthesis to the surgical instrument, as described below.

Within this disclosure, the terms horizontal and vertical are used to respectively describe the displacement of offset and leg length dimensions with respect to centers of head regions of different hip stem prostheses. Horizontal and vertical are used generally to delineate directions that are perpendicular to one another. Within the context of this disclosure, an indication of a vertical positioning corresponds to a proximal or distal positioning with respect to anatomical terminology. Further, an indication of a horizontal positioning corresponds to a medial or lateral positioning with respect to anatomical terminology.

Figure 1:
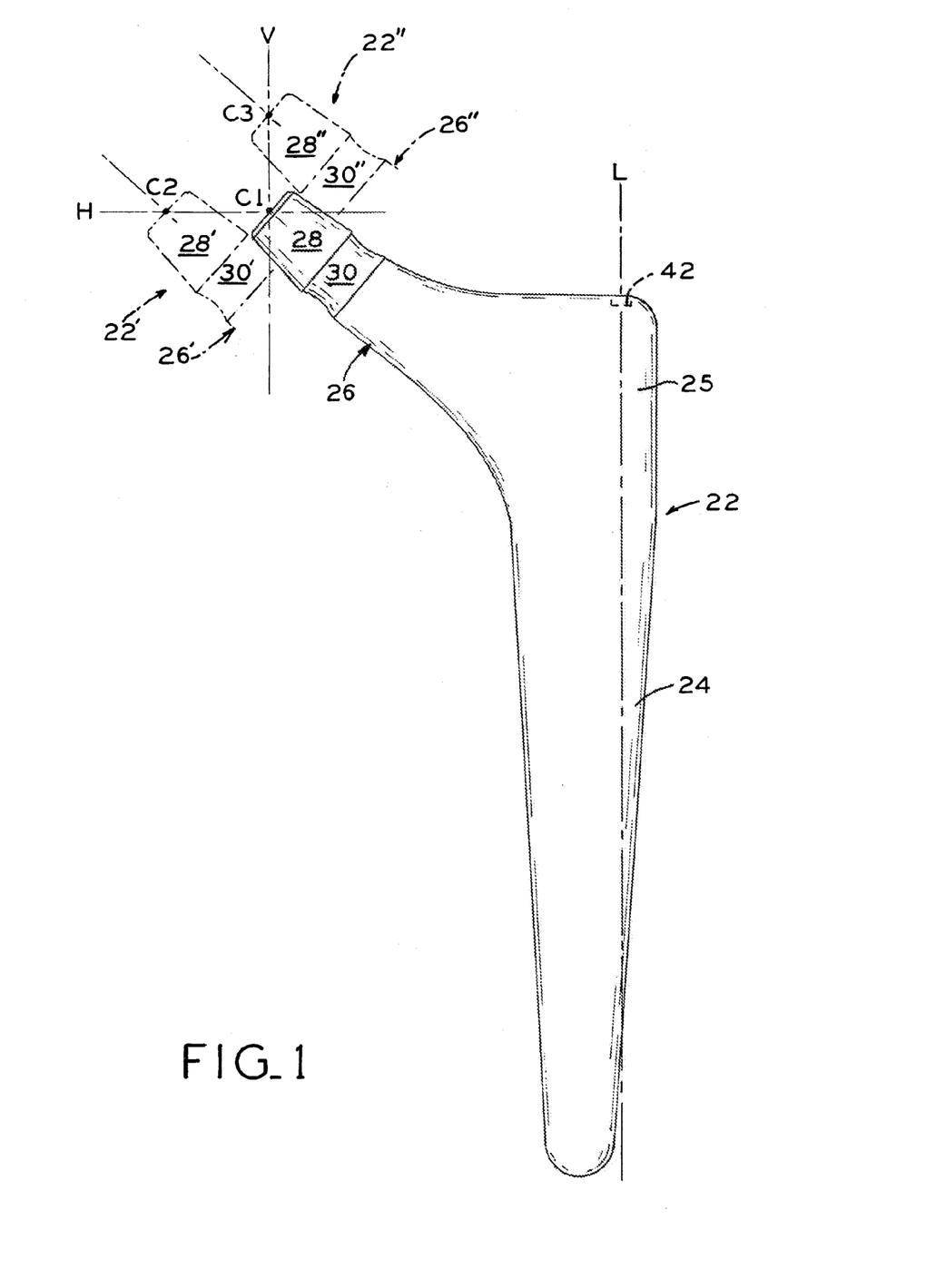
FIG. 1 is an elevational view of an exemplary hip stem prosthesis with ranging leg length and offset dimensions shown in dashed lines.

Referring to FIG. 1, exemplary hip stem prosthesis 22 is shown that includes stem portion 24, proximal body portion 25, and projecting neck portion 26. Particularly, neck portion 26 projects from proximal body portion 25, which is disposed above stem portion 24. Neck portion 26 includes head region 28 and tapered relief portion 30 below head region 28. Head region 28 is separated from stem portion 24 and proximal body portion 25 via tapered relief portion 30. Proximal body portion 25 and stem portion 24 include longitudinal axis L of prosthesis 22. An exemplary hip stem prosthesis is any hip stem prosthesis of the VerSys® Hip System manufactured and sold by Zimmer, Inc. of Warsaw, Ind.

FIG. 1 illustrates three different hip stem prostheses including substantially aligned longitudinal axes L such that a single longitudinal axis L will be referenced herein. The three different hip stem prostheses respectively include three different head centers C1, C2, and C3. For example, hip stem prosthesis 22 includes head region 28 (shown in solid lines) having head center C1. Hip stem prosthesis 22' includes head region 28' (shown in dashed lines) having head center C2 that is horizontally offset from head center C1, and horizontally offset with respect to longitudinal axis L, along axis or line H.

Further, hip stem prosthesis 22" includes head region 28" (shown in dashed lines) having head center C3. Head center C1 of hip stem prosthesis 22 (shown in solid lines) is vertically distanced from head center C3 of head region 28" of hip stem prosthesis 22" (shown in dashed lines) along axis or line V, that is substantially parallel to longitudinal axis L, indicating the different leg length dimensions of neck portions 26, 26" of the respective prostheses.

Figure 2:
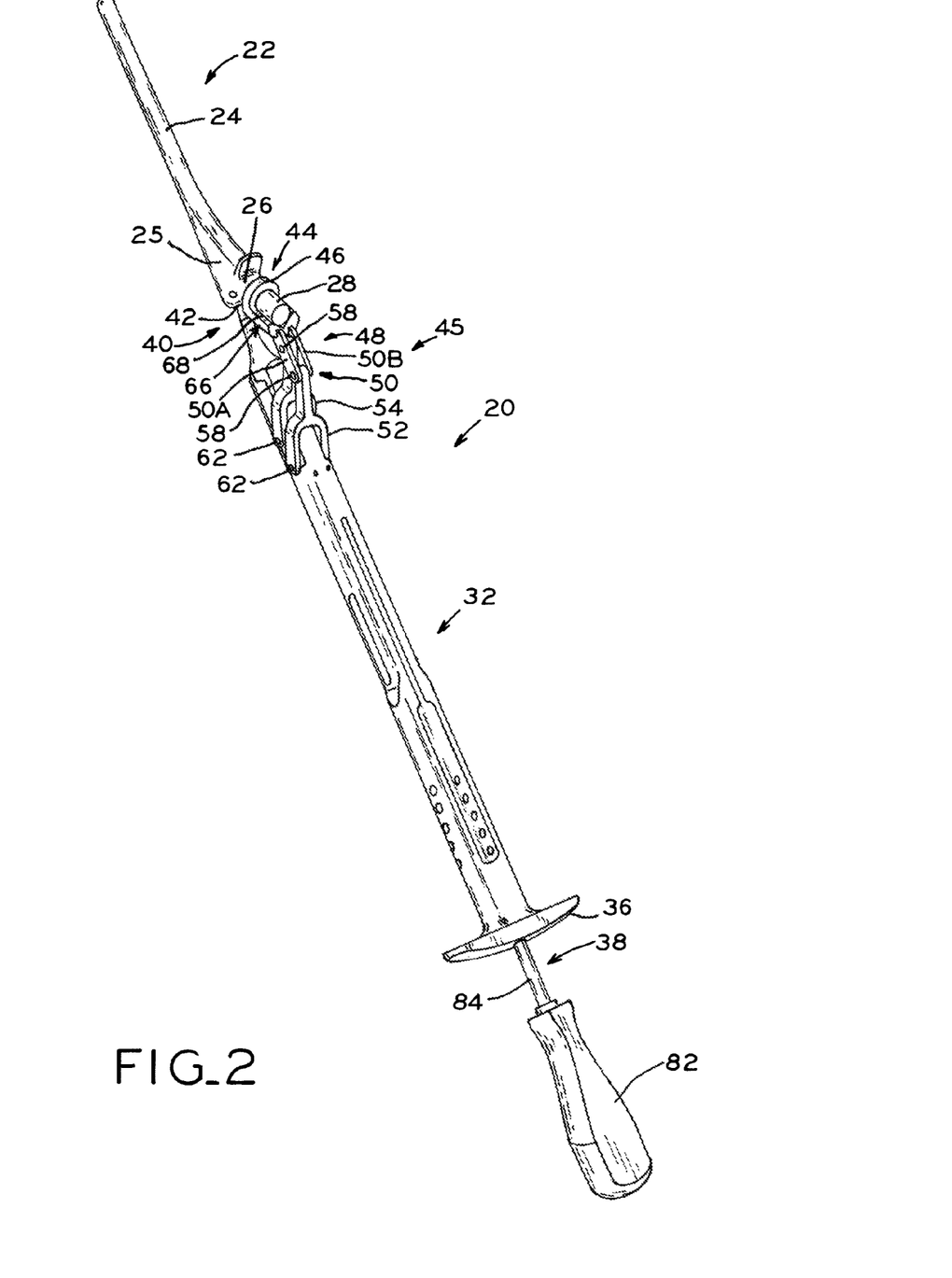
FIG. 2 is a perspective view of the surgical instrument of the present disclosure attached to a hip stem prosthesis via a first engagement portion that is an impaction portion and a second engagement portion that is a clamping portion.

Referring to FIG. 2, surgical instrument 20 is shown attached to hip stem prosthesis 22. Surgical instrument 20 includes body portion 32 having bore 34 (FIG. 3) extending through body portion 32. Driver 38 (FIGS. 2, 3, 5, and 6) may be inserted through bore 34 (FIG. 3) such that, as described further below, male hex end feature 86 of driver 38 matingly engages female hex end feature 88 of threaded rod 64 disposed in body portion 32 of surgical instrument 20.

When instrument 20 is secured to hip stem prosthesis 22, as described below, and driver 38 is removed from bore 34 of surgical instrument 20, surgical instrument 20 is usable as an impactor. Particularly, surgical instrument 20 includes impaction head 36 rigidly connected by body portion 32 to impaction portion 40. When driver 38 is disengaged from instrument 20, an impaction force applied on impaction head 36 translates along rigid body portion 32 to impaction portion 40. As impaction portion 40 is engaged with proximal body portion 25 of hip stem prosthesis 22, as described below, force is then translated from impaction portion 40 of instrument 20 to proximal body portion 25 of hip stem prosthesis 22. This force transmission allows for the impaction and seating of prosthesis 22 into a proximal femur (not shown), for example.

Surgical instrument 20 includes first engagement portion 40 projecting from body portion 32. First engagement portion 40 may be, for example, an impaction portion including a tip for receipt into impaction feature 42 on a top surface of proximal body portion 25. Impaction feature 42 may be, for example, an indent or a recess configured to receive the tip of impaction portion 40.

Surgical instrument 20 further includes second engagement portion 44 which may be, for example, a clamping portion that is movable with respect to body portion 32. Clamping portion 44 includes annular engagement member or collar 46 for engagement beneath head component 28 of hip stem prosthesis 22 and, in particular, for engagement with tapered relief section 30 of neck portion 26 of prosthesis 22.

Figure 3:
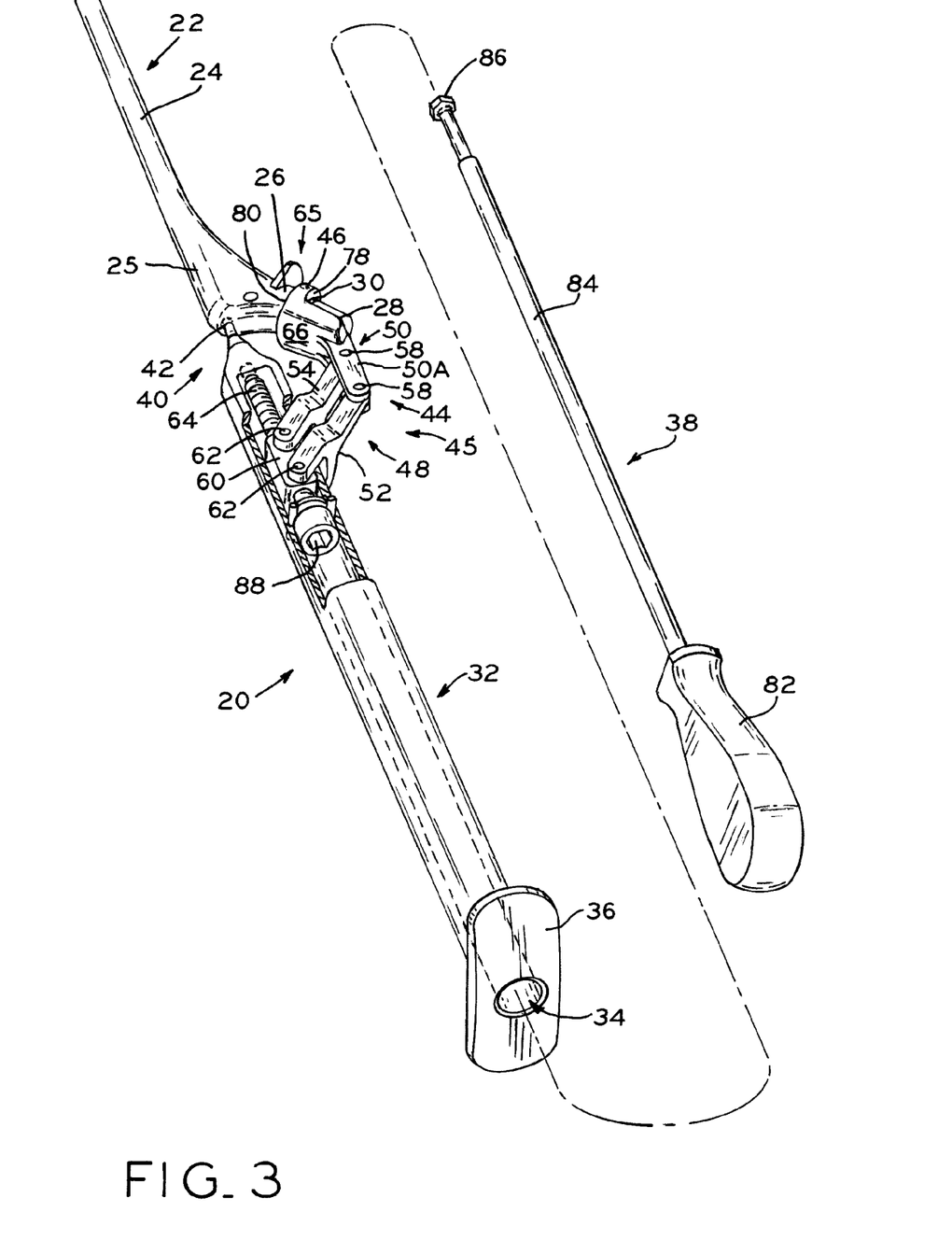
FIG. 3 is an exploded, perspective view of the surgical instrument attached to a hip stem prosthesis, showing an impaction head of the surgical instrument having a bore extending therethrough and a driver of the surgical instrument for insertion into the bore.
Figure 7:
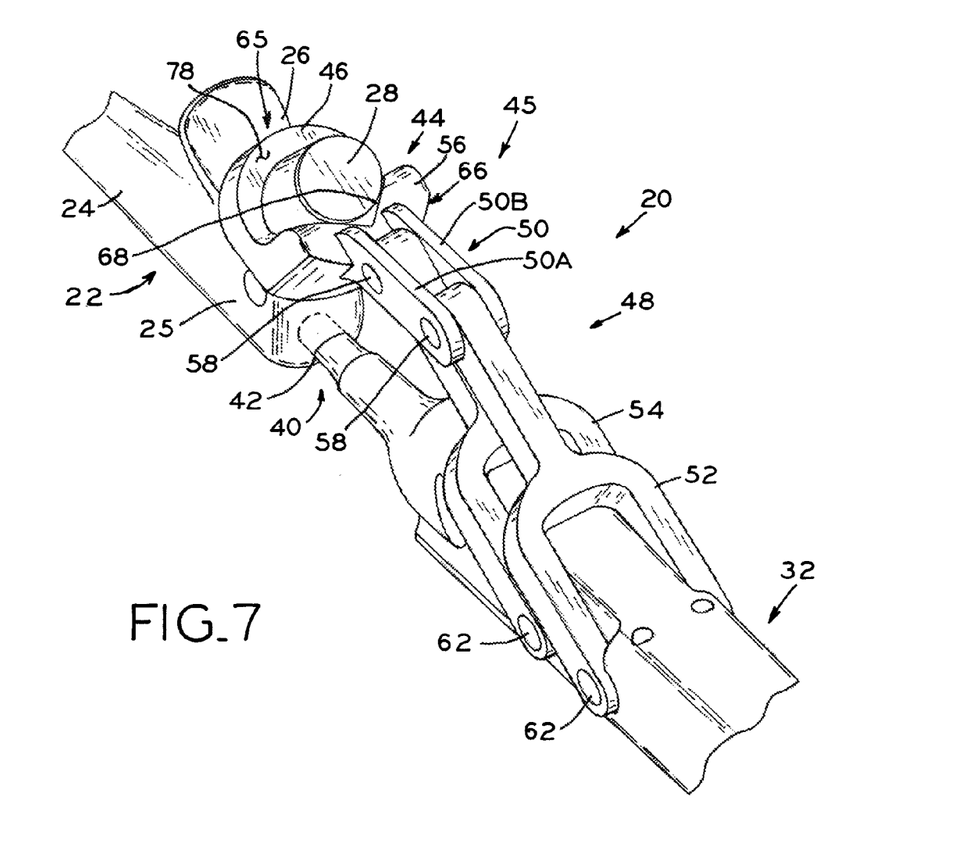
FIG. 7 is a fragmentary perspective view of impaction and clamping portions at the lower end of a body portion of the surgical instrument and their respective corresponding engagement to a proximal body portion and a neck portion of the hip stem prosthesis.

Referring to FIGS. 2 and 7, impaction portion 40 is shown received into indent 42 in a top surface of proximal body portion 25, and clamping portion 44 is shown engaging tapered relief section 30 beneath head region 28 of hip stem prosthesis 22. Clamping portion 44 is connected to body portion 32 via actuation assembly 45 which includes yoke assembly or linkage assembly 48, adjustment block 60 (FIG. 3), and threaded rod 64 (FIG. 3). Linkage assembly 48 of actuation assembly 45 forms a type of four-bar linkage between clamping portion 44 and adjustment block 60.

Figure 5:
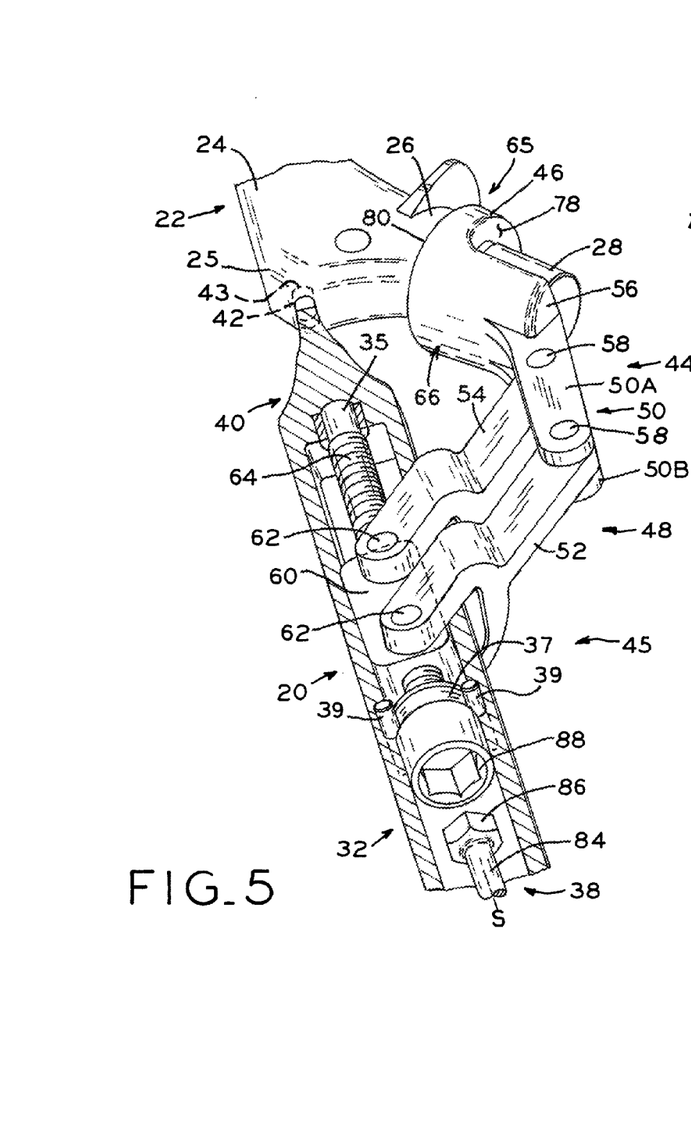
FIG. 5 is a fragmentary, perspective view of FIG. 3 after insertion of the driver into the surgical instrument bore, the driver having a male hex end feature at a distal end for engagement with a female hex end feature on a proximal portion of a threaded rod disposed within the body portion of the surgical instrument.
Figure 6:
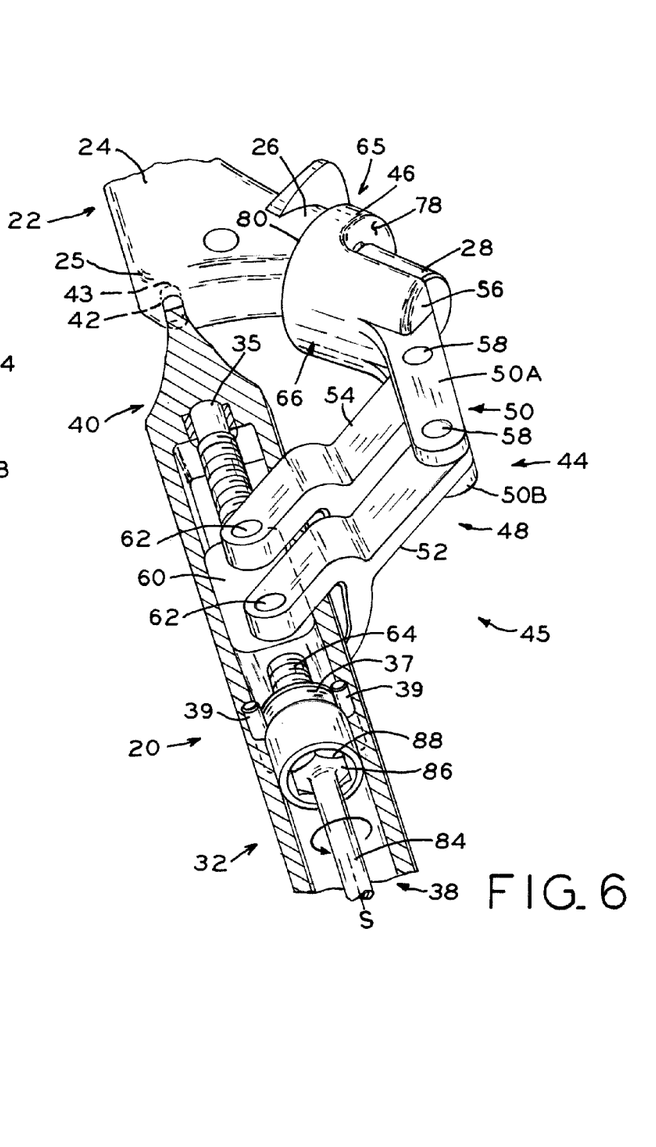
FIG. 6 is a fragmentary, perspective view of FIG. 3 showing the male hex end feature of the driver engaged with the female hex end feature of the threaded rod wherein rotational movement of the driver causes a corresponding rotation of the mating hex end feature that results in a longitudinal translation of an adjustment block with respect to the threaded rod.

Referring to FIGS. 5 and 6, linkage assembly 48 includes link lever 50 connected to two Y-shaped arms 52, 54. Each Y-shaped arm includes a lower bar from which two forked upper bars extend as prongs to create the Y-shape. Link lever 50 includes two opposing elongate plates 50A, 50B which project from top surface 56 of clamping portion 44 and are rotatably connected via pins 58 to upper Y-shaped arm 52 and lower Y-shaped arm 54. Pins 58 are received through apertures (not shown) extending through respective lower bars of arms 52, 54 and through plates 50A, 50B of link lever 50.

Figure 4:
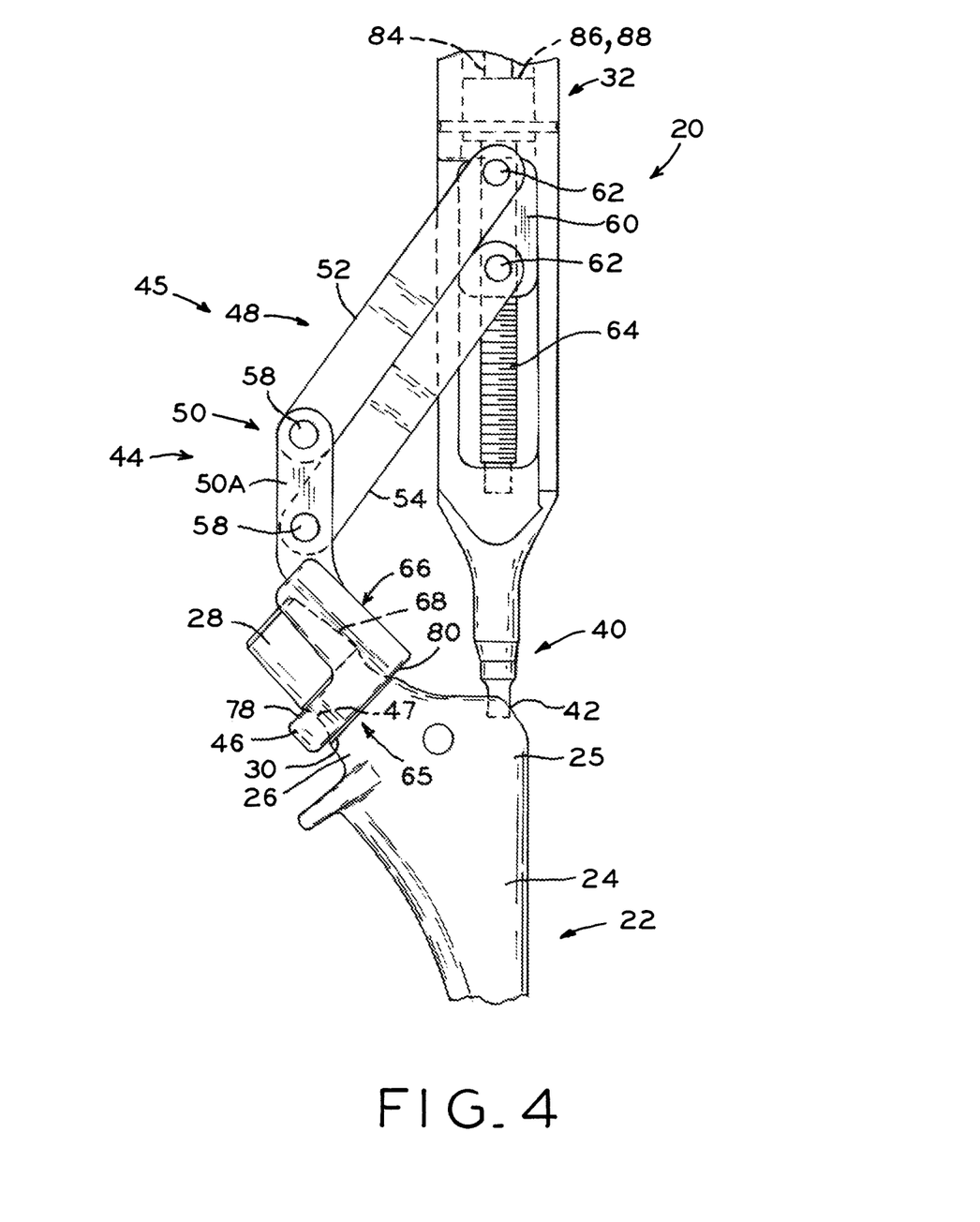
FIG. 4 is a fragmentary, elevational view of the surgical instrument of FIG. 2 attached to the hip stem prosthesis such that the impaction portion is attached to a proximal body portion of the hip stem prosthesis and the clamping portion is attached to a tapered relief portion of the neck portion beneath the head region of the hip stem prosthesis.

Upper arm 52 and lower arm 54 are pivotally connected to adjustment block 60 (FIGS. 3-6 and 13) via pins 62. Adjustment block 60 is exposed and accessible through slots defined by walls on opposite sides of body portion 32. Pins 62 are received through apertures (not shown) extending through upper bars of arms 52, 54 and through block 60. Adjustment block 60 is threadably connected to and longitudinally displaceable along threaded rod 64 (FIGS. 3-6 and 13), as described further below. FIG. 4 shows a view of the attachment of instrument 20 of this disclosure to hip stem prosthesis 22 with impaction portion 40 engaged with proximal body portion 25 of hip stem prosthesis 22 and clamping portion 44 clamping tapered relief portion 30 beneath head region 28 of neck portion 26 of hip stem prosthesis 22.

Referring back to FIGS. 5 and 6, a distal end of threaded rod 64 is received within bushing 35, which is disposed within a distal end wall partially defining bore 34 of surgical instrument 20. At a proximal end, female hex end feature 88 of threaded rod 64 includes annular groove 37 that receives pins 39 disposed within internal walls defining bore 34. With the above-described structure, threaded rod 64 is substantially prevented from axial displacement about longitudinal axis S of surgical instrument 20 while still being able to rotate about longitudinal axis S.

Figure 8:
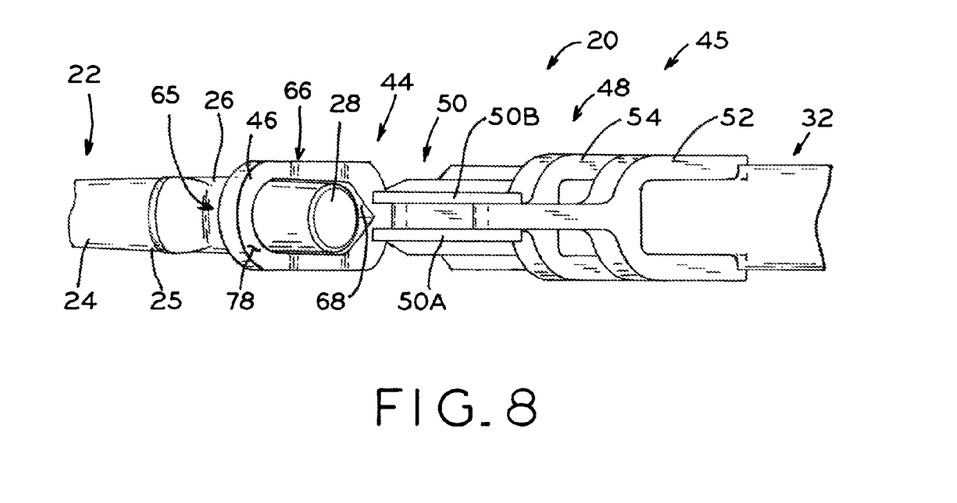
FIG. 8 is a front perspective view of the engagement shown in FIG. 7.

Referring to FIG. 8, clamping portion 44 includes front portion 65 including collar 46. Clamping portion 44 also includes rear portion 66 having second internal wall or rear wall 68 projecting transversely from collar 46. With collar 46 of clamping portion 44 received about tapered relief portion 30 of hip stem prosthesis 22, as shown in FIG. 8, rear wall 68 of rear portion 66 can contact head region 28 along at least two contact surfaces of rear wall 68 which, as shown herein, may be generally linear contact surfaces. For example, referring to FIGS. 9 and 10, the contact surfaces of rear wall 68 which contact head region 28 are shown as contact surface 70A and contact surface 70B.

Figure 9:
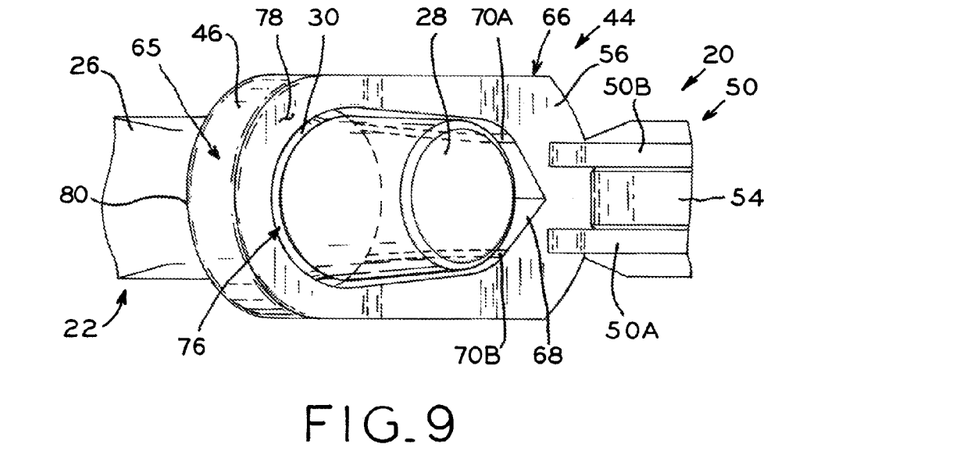
FIG. 9 is a fragmentary view of the engagement shown in FIG. 8, particularly showing a pair of flat surfaces of a rear wall of the clamping portion of the surgical instrument in engagement with the neck portion of the hip stem prosthesis.
Figure 10:
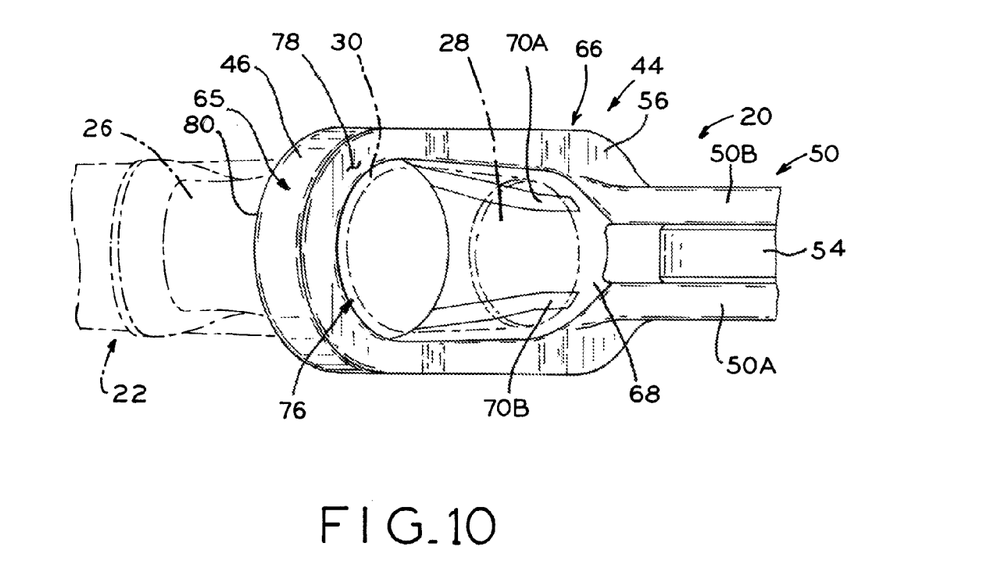
FIG. 10 is a fragmentary view of another embodiment of the surgical instrument with the neck portion shown in phantom.

The combination of the engagement of collar 46 of clamping portion 44 against tapered relief portion 30 of head region 28 and the contact of the two substantially flat surfaces 70A, 70B of rear wall 68 of clamping portion 44 with head region 28 allow for opposing clamping forces when instrument 20 is attached to prosthesis 22, as described further below. The opposing clamping forces prevent rocking of head region 28 within clamping portion 44 and provide rotational control of hip stem prosthesis 22 via surgical instrument 20.

FIG. 10 illustrates another embodiment of clamping portion 44 with prosthesis 22 shown in phantom. Clamping portion 44 does not include a V-shaped rear wall 68 but rather includes a more arcuately shaped rear wall. Rear wall 58 of FIG. 10 still includes contact surfaces 70A, 70B, though the surfaces are not shown to completely extend to a top of rear wall 68 (as shown in FIG. 9). Additionally, while contact surfaces 70A, 70B are generally indicated in the drawings, such exact lines may not be visually identifiable and marked in an actual surgical instrument 20.

Figure 11A:
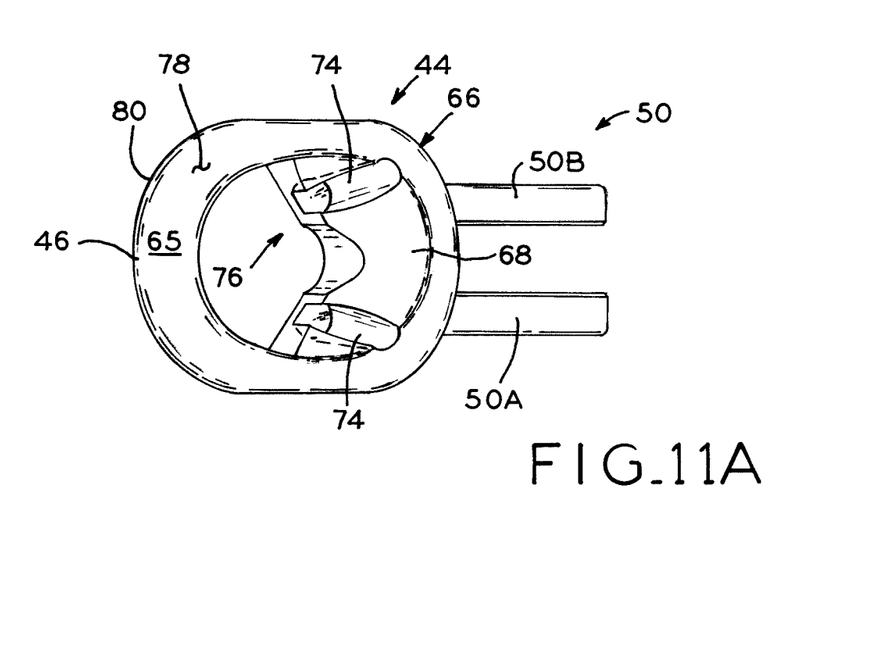
FIG. 11A is a perspective view of the clamping portion of the surgical instrument of the present disclosure separated from the remainder of the surgical instrument and including channels along an inner wall of the clamping portion.
Figure 11B:
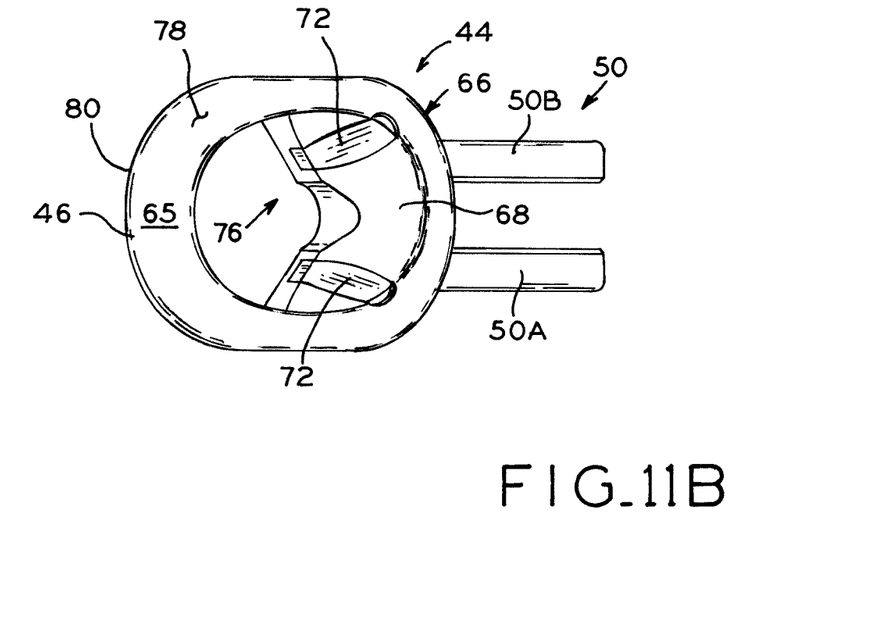
FIG. 11B a perspective view of the clamping portion of the surgical instrument of the present disclosure separated from the remainder of the surgical instrument and showing inserts received within the channels of FIG. 11A for contacting the neck/head component of the hip stem prosthesis of FIG. 2.

In an alternative embodiment, as shown in FIGS. 11A and 11B, contact surfaces 70A, 70B (FIGS. 9 and 10) of rear wall 68 are formed by inserts (FIG. 11B) that may be metallic or non-metallic inserts. Inserts 72 may be, for example, plastic inserts. As shown in FIG. 11B, inserts 72 are inserted or molded into channels 74 (FIG. 11A) within rear wall 68 of clamping portion 44.

Referring back to FIG. 4, surgical instrument 20 is shown attached to hip stem prosthesis 22 via attachment of impaction portion 40 and clamping portion 44 to hip stem prosthesis 22, as described above. Via actuation assembly 45, clamping portion 44 may adjustably connect to either a first neck portion of a first hip stem prosthesis or a second neck portion of a second hip stem prosthesis that has a different offset and/or leg length dimension than the first hip stem prosthesis.

Figure 12A:
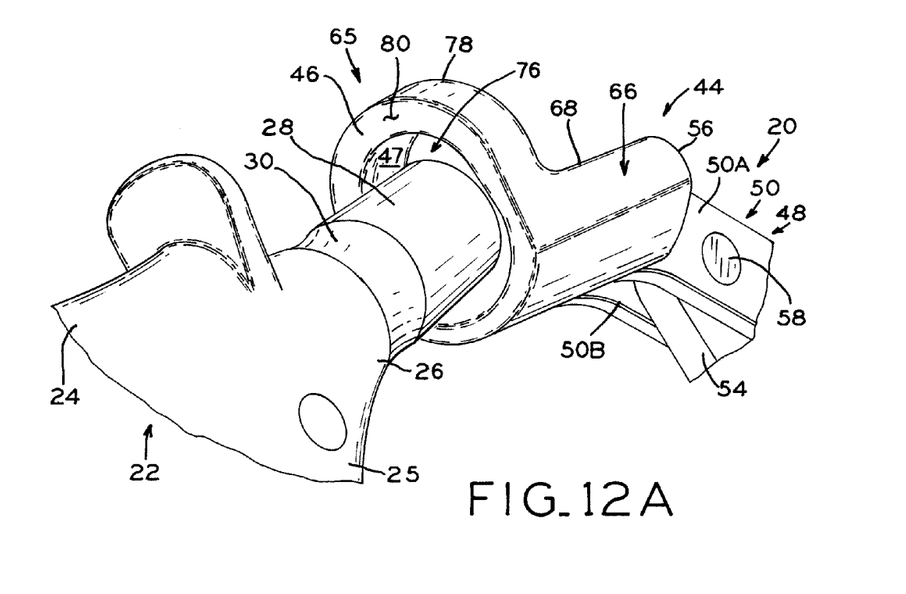
FIG. 12A is a fragmentary, perspective view of the clamping portion of the surgical instrument in a first position prior to engagement with the neck/head component of the hip stem prosthesis.
Figure 12B:
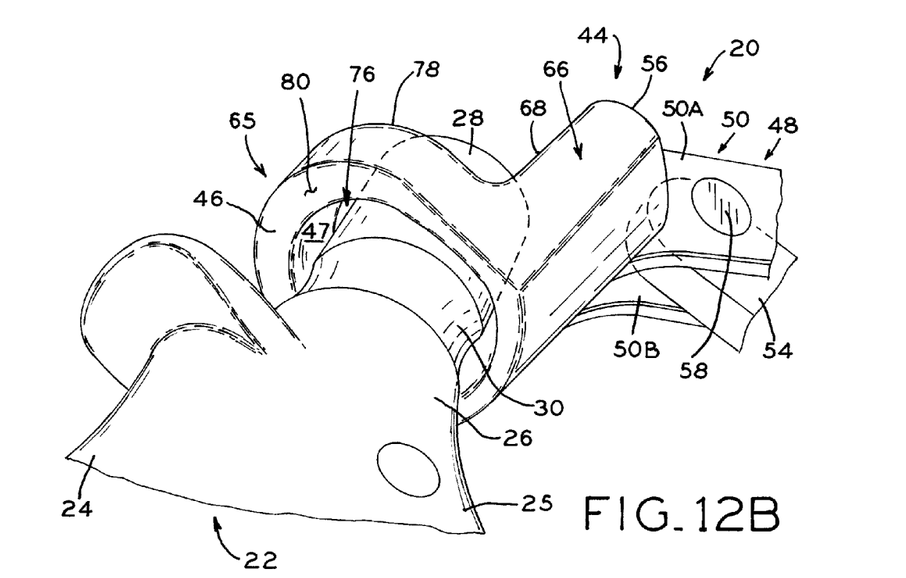
FIG. 12B is a fragmentary, perspective view of the clamping portion being rotated about a linkage assembly or link lever of the surgical instrument and being pushed into a downward position to engage with the neck portion of the hip stem prosthesis.

FIGS. 12A-12D illustrate how clamping portion 44 is attached to neck portion 26 of hip stem prosthesis 22. As shown in FIG. 12A, collar 46 of clamping portion 44 includes bore 76 extending from proximal surface 78 (FIGS. 9-10) to distal surface 80 (FIGS. 12A-12B) and formed by first internal wall or tapered relief wall 47 of collar 46. Prior to engaging impaction portion 40 of surgical instrument 20 with indent 42 of hip stem prosthesis 22, clamping portion 44 is first inserted over head region 28 such that head region 28 is loosely received in bore 76 of clamping portion 44. As shown in FIG. 12B, clamping portion 44 rotates about pins 58 on link lever 50 with respect to arm 52 (FIG. 4) and arm 54 (FIG. 12B) to which they are connected to downwardly position clamping portion 44 over head region 28 of hip stem prosthesis 22. In particular, collar 46 is pushed downward towards tapered relief portion 30 of neck portion 26 of hip stem prosthesis 22 beneath head region 28 and between head region 28 and proximal body portion 25.

Figure 12C:
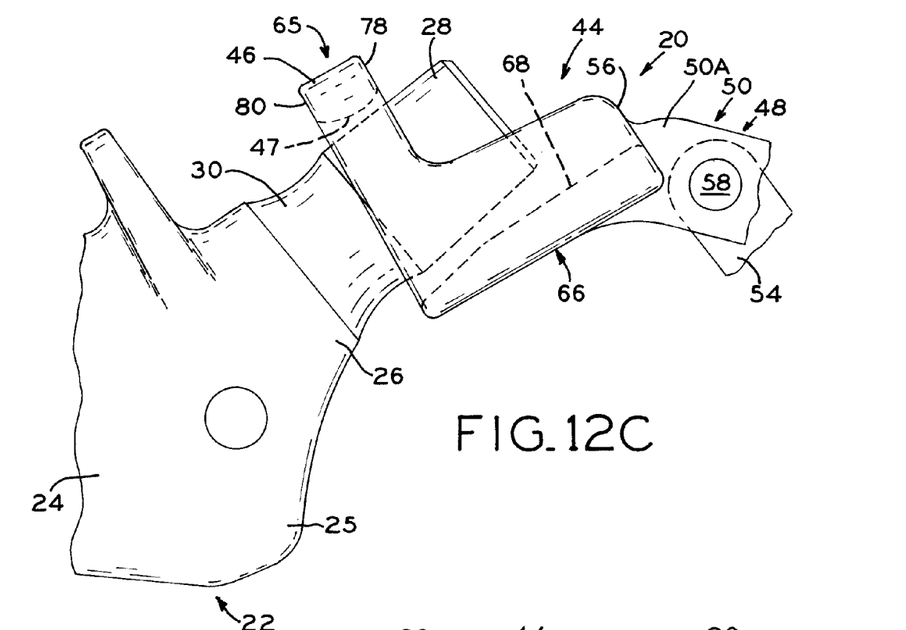
FIG. 12C is a fragmentary, side elevational view of the clamping portion of the surgical instrument about to be engaged with a tapered relief portion on the neck portion and beneath the head component of the hip stem prosthesis.
Figure 12D:
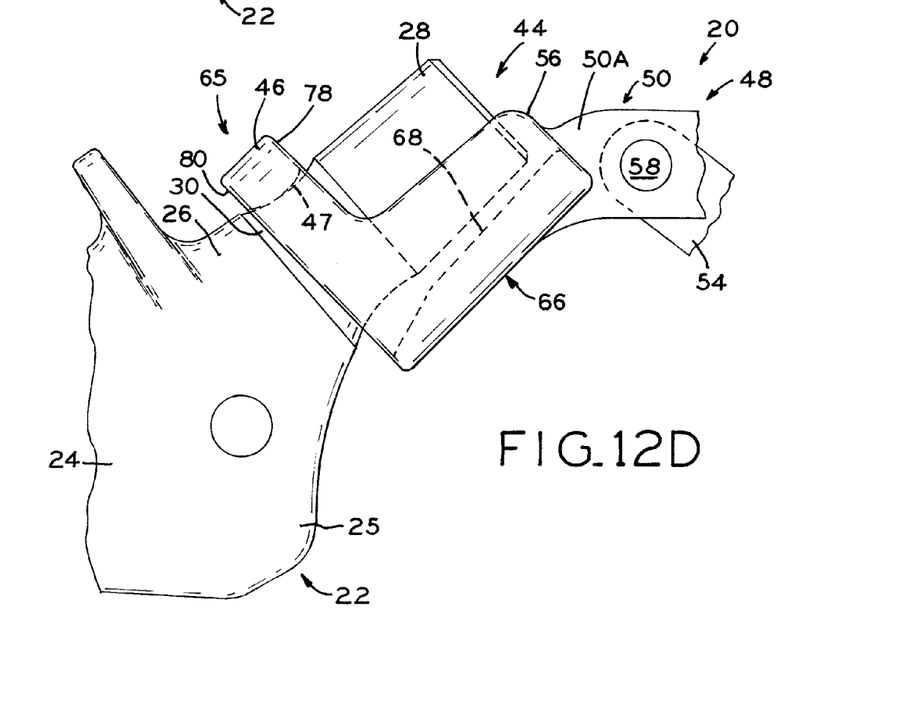
FIG. 12D is a fragmentary, elevational view of the engagement of the clamping portion of the instrument engaged with the tapered relief portion on the neck portion and beneath the head component of the hip stem prosthesis.

As shown in FIG. 12C, front portion 65 of clamping portion 44 includes tapered relief wall 47 of annular collar 46 that is shaped to abut against and clamp tapered relief portion 30 of neck portion 26. FIG. 12D shows clamping portion 44 engaged with tapered relief portion 30 of neck portion 26 of hip stem prosthesis 22. With surgical instrument 20 secured to prosthesis 22, head region 28 will also contact surfaces 70A, 70B (FIGS. 9 and 10) of rear wall 68 of clamping portion 44. If impaction portion 40 is disengaged from indent 42, clamping portion 44 may be removed from neck portion 26 by reversing the steps of insertion. For example, tapered relief wall 47 may be rotated away from contact with head region 28 and clamping portion 44 may be pulled away from and over head region 28 while tapered relief wall 47 clears head region 28 to allow for the withdrawal of clamping portion 44.

Pins 58 and 62 of this disclosure are rotatable within the apertures through which they are received as they may have an outer diameter that is less than the inner diameter of the respective apertures. Arms 52 and 54, for instance, may move and rotate about pins 62 connecting arms to block 60. As arms 52, 54 rotate about pins 62 and move with respect to adjustment block 60, link lever 50 additionally rotates about pins 58 connecting arms 52, 54 to link lever 50 in a similar manner. Particularly, as these pins are also rotatable, link lever 50 will rotate about pins 58 to move with respect to arms 52, 54 and thus clamping portion 44, integral with link lever 50, will move with respect to arms 52, 54 and body portion 32 of instrument 20.

As discussed above, FIG. 3 illustrates an exploded view of surgical instrument 20 where driver 38 is not yet inserted into body portion 32 of surgical instrument 20. Driver 38 includes handle end 82, rod 84 projecting from handle end 82, and male hex end feature 86. Male hex end feature 86 is configured to engage with mating female hex end feature 88 disposed at a top, proximal end of threaded rod 64. As shown in FIG. 5, when driver 38 is inserted into bore 34 of instrument 20 to substantially extend a majority of the length of body portion 32, male hex end feature 86 is disposed above female hex end feature 88. Male hex end feature 86 will be inserted into female hex end feature 88 until the hex end features 86 and 88 are matingly engaged, as shown in FIG. 6. Upon such engagement, driver 38 may be rotated in the direction of arrow A (FIG. 6), which causes a corresponding rotation of threaded rod 64. The rotation of threaded rod 64 will cause translation of adjustment block 60 that is constrained against rotation about and threadably engaged to threaded rod 64. For example, should the rotation occur in a clockwise direction, block 60 will translate upward on threaded rod 64. Should the rotation occur in a counter-clockwise direction, block 60 will translate or move in a downwards direction on the threaded rod 64.

Referring to FIGS. 6 and 12A, when driver 38 is rotated in a selected direction, such as in the direction of arrow A (FIG. 6), adjustment block 60 will move longitudinally with respect to threaded rod 64. As further described below, when impaction portion 40 is received within indent 42, rotation of driver 38 in a clockwise direction will allow impaction portion 40 to tightly anchor to and be seated within indent 42 of proximal body portion 25. A counter-clockwise rotation will allow for impaction portion 40 to be loosened from such an engagement and to eventually be removed from indent 42.

A surgeon may position impaction portion 40 away from hip stem prosthesis 22 while loosely engaging clamping portion 44 to head region 28, as described above. The surgeon may then adjust impaction portion 40 until it is substantially aligned with indent 42. Particularly, a surgeon adjusts impaction portion 40 towards indent 42. If adjustment block 60 is positioned in a first position with respect to threaded rod 64, however, the surgeon may not be able to effect such an alignment of impaction portion 40 and indent 42 while clamping portion 44 is loosely engaged to neck portion 46 of hip stem prosthesis 22. The surgeon will then adjust adjustment block 60 to a desired position via driver 38, as described above, which is a position determined by trial and error by the surgeon, until the surgeon is able to align impaction portion 40 to be loosely received into indent 42 of hip stem prosthesis 22.

Via rotation of driver 38 in the direction of arrow A (FIG. 6), and described above, corresponding rotation of threaded rod 64 allows impaction portion 40 to be finally seated and anchored within indent 42, to provide a fixed, anchoring point while simultaneously actuation assembly 45 causes clamping portion 44 to tilt about tapered relief wall 47, urging rear wall 68 into engagement with head region 28, as described above. Particularly, as driver 38 is rotated clockwise, adjustment block 60 translates upwards, causing clamping portion 44 via actuation assembly 45, as described above, to be urged upwards against a distal surface of head region 28. Simultaneously, a downwards reaction force presses impaction portion 40 against distal wall 43 forming indent 42. While clamping portion 44 is being urged upwards against head region 28, it is also tilting inwardly towards body portion 32 of surgical instrument 20, causing opposing reaction forces that are transverse to axis S of surgical instrument 20 to occur against the contact points of neck portion 26 (namely along tapered relief wall 47 and contact surfaces 70A and 70B) and clamping portion 44 to firmly press clamping portion 44 to neck portion 26 of prosthesis 22. The resultant forces, as described above, act as binding forces to secure surgical instrument 20 against hip stem prosthesis 22.

Figure 13:
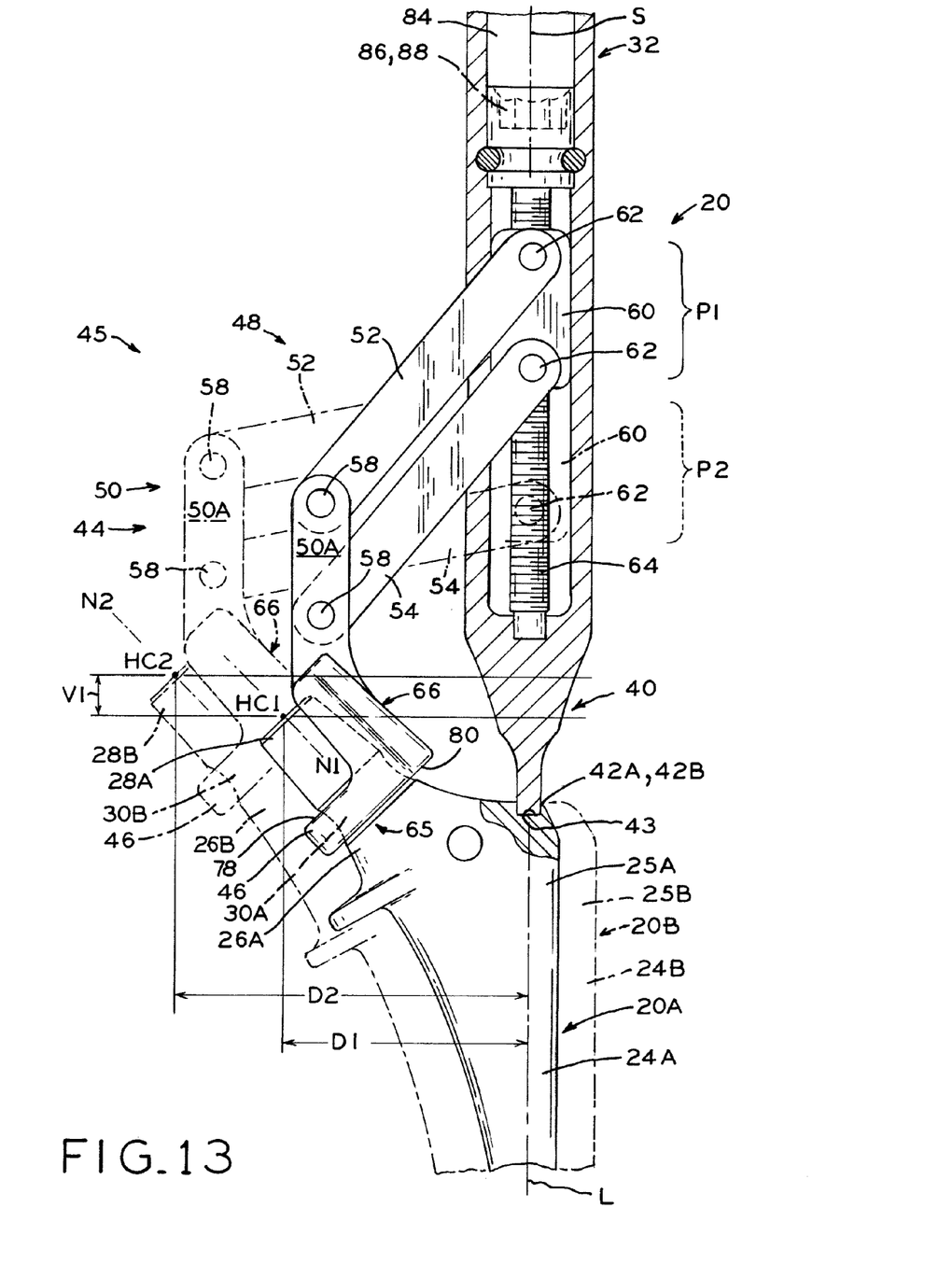
FIG. 13 schematically shows the surgical instrument of the present disclosure attached to hip stem prostheses of two different sizes, one shown in solid lines and the other in dashed lines, the prostheses having two different leg length and offset dimensions.

Referring to FIG. 13, an overall operation of surgical instrument 20 will be described. Particularly, FIG. 13 is a schematic representation illustrating the attachment of surgical instrument 20 to a first hip stem prosthesis 22A (shown in solid lines) and to an alternative second hip stem prosthesis 22B (shown in dashed lines). Second hip stem prosthesis 22B is a prosthesis having a longer leg length dimension and a larger offset dimension than first hip stem prosthesis 22A.

First hip stem prosthesis 22A includes head center HC1 horizontally spaced from longitudinal axis L, as shown via dimension D1. Head center HC1 intersects neck axis N1 of neck portion 26A of first hip stem prosthesis 22A.

Second hip stem prosthesis 22B includes head center HC2 horizontally spaced from longitudinal axis L, as shown via dimension D2. Head center HC2 intersects neck axis N2 of neck portion 26B of second hip stem prosthesis 22B.

Dimensions D1 and D2 depict the different respective offset dimensions of prostheses 22A and 22B. Prostheses 22A and 22B also have different leg length dimensions, which is indicated by head center HC2 of second hip stem prosthesis 22B being vertically spaced from head center HC1 of first hip stem prosthesis 22A at a distance shown as dimension V1. Moreover, indents 42A, 42B may be disposed in substantially the same location on the differently sized hip stem prostheses 22A, 22B and in substantial alignment with longitudinal axis L of each prosthesis.

The attachment of surgical instrument 20 to either first hip stem prosthesis 22A or second hip stem prosthesis 22B is described below. As described above, clamping portion 44 will loosely attach to neck portion 26A of first hip stem prosthesis 22A or neck portion 26B of second hip stem prosthesis 22B before impaction portion 40 is seated within respective indent 42A, 42B of the selected prosthesis. A surgeon may bring axis S of surgical instrument 20 into substantial alignment with axis L of the selected hip stem prosthesis 22A or 22B, through a trial and error method as described above that may require the surgeon to adjust the position of adjustment block 60 via driver 38. The surgeon then uses driver 38, as described above, to seat impaction portion 40 within respective indent 42A or 42B.

When clamping portion 44 is attached to first neck portion 26A of first hip stem prosthesis 22A and impaction portion 40 is moved into substantial alignment with indent 42A, block 60 has generally been adjusted by the surgeon to position P1 (shown in solid lines). Alternatively, when clamping portion 44 is attached to second neck portion 26B of second hip stem prosthesis 22B and impaction portion 40 is moved into substantial alignment with indent 42B, block 60 has generally been adjusted by the surgeon to position P2 (shown in dashed lines). The further that clamping portion 44 horizontally and/or vertically extends to accommodate respective offset and leg length dimensions, the lower block 60 will tend to be positioned with respect to threaded rod 64 when impaction portion 40 is brought into substantial alignment with the indent of the selected hip prosthesis.

When surgical instrument 20 is secured to the selected hip component 22A or 22B, as described above, the surgeon using the instrument is provided with substantially 360° of rotational control such that the surgeon may insert selected prosthesis 22A or 22B with substantial ease through multiple locations on the leg or body of a patient. For example, the surgeon may now insert the prosthesis through a posterior incision on the body of the patient, rather than an anterior incision, and then rotate the prosthesis into the desired orientation and position such that the prosthesis may be properly inserted into a prepared opening within the proximal end of the femur.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A surgical instrument for use with a prosthesis, comprising:
   a body having a bore extending through at least a portion of the body, the bore defining a longitudinal axis;
   a first engagement portion external to, and extending from, the body, the first engagement portion aligned substantially along a first axis;
   a second engagement portion configured to encircle a neck portion of a prosthesis, the second engagement portion external to the body and spaced from one or both of the longitudinal axis or the first axis;
   an adjustment arm having a first end and a second end, opposite the first end, the first end of the adjustment arm pivotally attached to the second engagement portion;
   an adjustment block disposed within the bore, the second end of the adjustment arm pivotally attached to the adjustment block; and
   a threaded rod configured to rotate about the longitudinal axis adjustment block threadingly connected to, and longitudinally displaceable along, the threaded rod,
   wherein the first engagement portion and the second engagement portion are disposed to contemporaneously engage, respectively, a proximal body portion and the neck portion of the prosthesis.

2. The surgical instrument of claim 1, wherein the adjustment block is movable through the bore, along the longitudinal axis, to vary the spacing of the second engagement portion from one or both of the longitudinal axis or the first axis.

3. The surgical instrument of claim 1, wherein the threaded rod is configured to rotate about the longitudinal axis without being axially displaced along the longitudinal axis.

4. The surgical instrument of claim 3, further comprising a driver receivable within the bore, the driver configured to engage the threaded rod to move the adjustment block longitudinally through the bore.

5. The surgical instrument of claim 1, wherein the second engagement portion comprises a collar portion and a projecting wall portion, extending transversely from the collar portion, the collar portion and the projecting wall portion cooperating to define a collar bore.

6. The surgical instrument of claim 5, wherein the collar portion includes a first internal wall configured to contact a first region of the neck portion and the projecting wall portion includes a second internal wall configured to contact a second region of the neck portion, opposite the first region, the second region being superior or inferior to the first region.

7. The surgical instrument of claim 6, wherein the first internal wall comprises one of a linear wall or a curved wall, and the second internal wall comprises the other of a linear wall or a curved wall.

8. The surgical instrument of claim 6, wherein the first region is a tapered region of the neck portion and the second region is a head region of the neck portion, opposite the tapered region, the head region being superior to the tapered region.

9. The surgical instrument of claim 7, wherein the first internal wall comprises a curved wall, the curve radially extending into the collar bore, and the second internal wall comprises a linear wall.

10. The surgical instrument of claim 7, wherein the linear wall includes a first and a second planar segment disposed at an angle to each other.

11. The surgical instrument of claim 7, wherein the curved wall and the linear wall cooperate to provide opposing clamping forces to clamp the second engagement portion to the neck portion of the prosthesis.

12. The surgical instrument of claim 1, the body further including a wall defining at least one slot, the adjustment block accessible through the at least one slot for pivotal attachment to the second end of the adjustment arm.

13. The surgical instrument of claim 1, wherein the second engagement portion comprises a clamping portion and a lever, the first end of the adjustment arm pivotally attached to the lever.

14. The surgical instrument of claim 1, wherein a distal end of the threaded rod is configured to be received within a bushing disposed in a distal end wall of the bore.

15. The surgical instrument of claim 1, wherein a proximal end of the threaded rod is fixedly attached to an internal wall of the bore.

16. The surgical instrument of claim 1, further comprising a driver receivable within the bore, the driver configured to engage the threaded rod to move the adjustment block longitudinally along the threaded rod.

17. The surgical instrument of claim 1, further comprising a driver, wherein a proximal end of the threaded rod comprises one of a male or a female hex feature, and a distal end of the driver comprises the other of a male or a female hex feature, the male and the female hex features configured to engage each other to move the adjustment block longitudinally along the threaded rod.

* * * * *